US010647888B2

(12) United States Patent
Ando et al.

(10) Patent No.: US 10,647,888 B2
(45) Date of Patent: May 12, 2020

(54) 2-CYANOACRYLATE ADHESIVE COMPOSITION

(71) Applicant: TOAGOSEI CO., LTD., Tokyo (JP)

(72) Inventors: Masaru Ando, Nagoya (JP); Norifumi Yoshida, Nagoya (JP); Hiroyuki Terai, West Jefferson, OH (US)

(73) Assignee: Toagosei Co., LTD., Tokyo (JP)

( * ) Notice: Subject to any disclaimer, the term of this patent is extended or adjusted under 35 U.S.C. 154(b) by 0 days.

(21) Appl. No.: 15/551,535

(22) PCT Filed: Feb. 18, 2016

(86) PCT No.: PCT/JP2016/054736
§ 371 (c)(1),
(2) Date: Aug. 16, 2017

(87) PCT Pub. No.: WO2016/133166
PCT Pub. Date: Aug. 25, 2016

(65) Prior Publication Data
US 2018/0037772 A1 Feb. 8, 2018

(30) Foreign Application Priority Data
Feb. 18, 2015 (JP) .................................. 2015-029364

(51) Int. Cl.
C09J 4/00 (2006.01)
C09J 11/06 (2006.01)
C09J 11/08 (2006.01)
C07C 255/08 (2006.01)
C08F 222/32 (2006.01)
C08L 23/08 (2006.01)
C09J 123/04 (2006.01)

(52) U.S. Cl.
CPC .............. C09J 4/00 (2013.01); C07C 255/08 (2013.01); C08F 222/32 (2013.01); C08L 23/0869 (2013.01); C09J 11/06 (2013.01); C09J 11/08 (2013.01); C09J 123/04 (2013.01)

(58) Field of Classification Search
CPC ..... C09J 4/00; C09J 11/06; C09J 11/08; C09J 123/04; C07C 255/08; C08F 222/32; C08L 23/0869
See application file for complete search history.

(56) References Cited

U.S. PATENT DOCUMENTS

| 4,339,457 A | 7/1982 | Plummer et al. |
| 4,450,265 A * | 5/1984 | Harris ........................ C09J 4/00 |
| | | 526/204 |
| 4,695,615 A | 9/1987 | Leonard et al. |
| 2008/0314519 A1 | 12/2008 | Attarwala et al. |
| 2011/0251318 A1 * | 10/2011 | Ishizaki ..................... C09J 4/00 |
| | | 524/208 |
| 2014/0124137 A1 | 5/2014 | Hedderman et al. |
| 2014/0262021 A1 | 9/2014 | Goff et al. |

FOREIGN PATENT DOCUMENTS

| EP | 0690112 A1 | 1/1996 |
| JP | S52-078933 A | 7/1977 |
| JP | S55-2236 B2 | 1/1980 |
| JP | S57-501529 A | 8/1982 |
| JP | S57-501629 A | 9/1982 |
| JP | S58-008771 A | 1/1983 |
| JP | S60-168775 A | 9/1985 |
| JP | S60-179482 A | 9/1985 |
| JP | S62-235379 A | 10/1987 |
| JP | S63-088512 A | 4/1988 |
| JP | S63-128088 A | 5/1988 |
| JP | H01-182385 A | 7/1989 |
| JP | H02-020581 A | 1/1990 |
| JP | H03-167279 A | 7/1991 |
| JP | H06-057214 A | 3/1994 |
| JP | H07-97550 A | 4/1995 |
| JP | 2000-191600 A | 7/2000 |
| JP | 2009-500517 A | 1/2009 |
| JP | 2014-522899 A | 9/2014 |
| WO | 2014/140798 A2 | 9/2014 |

OTHER PUBLICATIONS

International Search Report for PCT/JP2016/054736 dated May 10, 2016, with English translation, (5 pages).
Written Opinion of the International Search Authority, dated Aug. 25, 2016, for PCT/JP2016/054736.
Extended European Search Report, dated Oct. 4, 2018, in EP appln. 16 75 2552.
PRC First Office Action against corresponding CN patent application 201680010659.2, dated Jan. 20, 2020, English translation submitted herewith.

* cited by examiner

*Primary Examiner* — John E Uselding
(74) *Attorney, Agent, or Firm* — Fitch, Even, Tabin & Flannery, LLP

(57) ABSTRACT

Provided is an adhesive composition which exhibits excellent water resistance and warm-water resistance without impairing instantaneous adhesiveness. The 2-cyanoacrylate adhesive composition contains a 2-cyanoacrylic acid ester, and a specific phthalic anhydride derivative, in which the content of the phthalic anhydride derivative is from 0.01 to 5% by mass, relative to the total amount of the adhesive composition. Preferably, the adhesive composition further contains an elastomer.

20 Claims, No Drawings

2-CYANOACRYLATE ADHESIVE COMPOSITION

CROSS-REFERENCE TO RELATED APPLICATIONS

This application is a U.S. national phase application filed under 35 U.S.C. § 371 of International Application No. PCT/JP2016/054736, filed Feb. 18, 2016, designating the United States, which claims priority from Japanese Patent Application No. 2015-029364, filed Feb. 18, 2015, and the complete disclosures of such applications are hereby incorporated herein by reference in their entirety for all purposes.

TECHNICAL FIELD

The present invention relates to a 2-cyanoacrylate adhesive composition. More specifically, the present invention relates to an adhesive composition containing a 2-cyanoacrylic acid ester, which exhibits excellent water resistance and warm-water resistance without impairing curability.

BACKGROUND ART

The 2-cyanoacrylate adhesive composition quickly establishes a strong bonding between various types of materials attributed to the unique anion polymerization characteristics exhibited by its principal component, 2-cyanoacrylic acid ester, which initiates polymerization under the presence of weak anion provided by slight moisture or the like attached to a surface of an adherend. Accordingly, it is used as the so-called instantaneous adhesive in a wide range of fields including industrial, medical, and household applications. However, because this adhesive composition is inferior in heat resistance and water resistance, there is a problem of lowering the adhesion strength when bonded articles are used under a severe environment.

To overcome these problems, modification methods have been proposed heretofore, which include adding various types of additives. For example, Patent Document 1 discloses an adhesive composition which comprises a 2-cyanoacrylic acid ester to which at least one compound selected from aromatic polycarboxylic acids and anhydrides thereof is added. Furthermore, Patent Document 2 discloses phthalic anhydride as a specific additive that improves adhesion durability under humid or high temperature environment. Further, Patent Document 3 discloses a cyanoacrylate adhesive composition which contains a 2-cyanoacrylic acid ester and a hydrogenated anhydride to improve heat resistance.

CONVENTIONAL TECHNICAL DOCUMENTS

Patent Documents

Patent Document 1: Japanese Patent Publication (Laid-open) No. S52-78933.
Patent Document 2: Japanese Patent Publication (Laid-open) No. S57-501529.
Patent Document 3: Japanese Patent Publication (Laid-open) No. 2014-522899.

SUMMARY OF INVENTION

Problems to be Solved by the Invention

Although the aromatic polycarboxylic acid disclosed in Patent Document 1 improves heat resistance, it is still unsatisfactory in that the curing rate of the adhesive composition is lowered due to the acidity thereof. Further, the acid anhydrides such as phthalic anhydride described in Patent Documents 1 and 2 improve heat resistance, but do not improve water resistance or warm-water resistance sufficiently. Furthermore, the hydrogenated anhydride disclosed in Patent Document 3 also improves heat resistance, but does not provide sufficient warm-water resistance.

The present invention has been made in light of the above described circumstances, and the objective thereof is to provide an adhesive composition containing a 2-cyanoacrylic acid ester, which exhibits excellent water resistance and warm-water resistance without impairing curability.

Means for Solving the Problems

The present inventors have made diligent studies for solving the aforementioned problems, and as a result, have found that an adhesive composition containing a 2-cyanoacrylic acid ester and a specific phthalic anhydride derivative possesses curability, water resistance and warm-water resistance in combination. Thus, the present invention has been accomplished.

That is, the present invention according to one aspect thereof provides a 2-cyanoacrylate adhesive composition containing (a) a 2-cyanoacrylic acid ester and (b) a phthalic anhydride derivative represented by the following general formula (1), wherein the content of the phthalic anhydride derivative is from 0.01 to 5% by mass relative to the total amount of the adhesive composition.

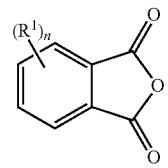

(1)

wherein $R^1$ is an alkyl group, acyl group, acyloxy group, aryloxycarbonyl group, aryl group, hydroxyl group, chlorine atom, bromine atom or iodine atom, and n represents an integer of 1 to 4.

According to the preferable embodiment of the present invention, the present 2-cyanoacrylate adhesive composition further comprises an elastomer (c), in which the content of the elastomer is from 1 to 30% by mass relative to the total amount of the adhesive composition.

According to a more preferable embodiment of the present invention, the elastomer (c) is a copolymer made from a monomer capable of forming a polymer poorly soluble to 2-cyanoacrylic acid ester and a monomer capable of forming a polymer soluble to 2-cyanoacrylic acid ester.

According to still another preferable embodiment of the present invention, the elastomer (c) is a copolymer made from a monomer capable of forming a polymer poorly soluble to 2-cyanoacrylic acid ester, a monomer capable of forming a polymer soluble to 2-cyanoacrylic acid ester, and a monomer containing a carboxyl group.

According to a furthermore preferable embodiment of the present invention, the monomer capable of forming a polymer poorly soluble to 2-cyanoacrylic acid ester is at least one selected from the group consisting of ethylene, propylene, isoprene and butadiene, and the monomer capable of forming a polymer soluble to 2-cyanoacrylic acid ester is at least one selected from the group consisting of acrylic acid esters and methacrylic acid esters.

Effect of the Invention

The 2-cyanoacrylate adhesive composition according to the present invention contains a 2-cyanoacrylic acid ester, and a phthalic anhydride derivative having a specific structure, and thus can provides a cured product excellent in water resistance and warm-water resistance without impairing instantaneous curability upon adhesion.

When the adhesive composition further contains an elastomer, the resulting cured product is further improved in warm-water resistance.

DESCRIPTION OF EMBODIMENTS

One embodiment of the present invention is described as follows, however, the present invention is not limited to those.

The 2-cyanoacrylate adhesive composition according to the present invention (hereinafter often simply referred to as "adhesive composition") is an adhesive composition which comprises (a) a cyanoacrylic acid ester, and (b) a phthalic anhydride derivative having a specific structure in specific amounts thereof.

As the above-mentioned "(a) a cyanoacrylic acid ester", any 2-cyanoacrylic acid ester that has generally been used in this type of adhesive composition can be used without any limitation. The 2-cyanoacrylic acid ester includes, for instance, methyl, ethyl, chloroethyl, n-propyl, i-propyl, allyl, propargyl, n-butyl, i-butyl, n-pentyl, n-hexyl, cyclohexyl, phenyl, tetrahydrofurfuryl, heptyl, 2-ethylhexyl, n-octyl, 2-octyl, n-nonyl, oxononyl, n-decyl, n-dodecyl, methoxyethyl, methoxypropyl, methoxyisopropyl, methoxybutyl, ethoxyethyl, ethoxypropyl, ethoxyisopropyl, propoxymethyl, propoxyethyl, isopropoxyethyl, propoxypropyl, butoxymethyl, butoxyethyl, butoxypropyl, butoxyisopropyl, butoxybutyl, 2,2,2-trifluoroethyl, and hexafluoroisopropyl esters of 2-cyanoacrylic acid. Preferred among them from the viewpoint of obtaining adhesive compositions with improved curability are alkyl 2-cyanoacrylates having an alkyl group containing from 1 to 4 carbon atoms. These 2-cyanoacrylic acid esters may be used alone or in a combination of two or more thereof.

The adhesive composition according to the present invention contains "(b) a phthalic anhydride derivative" represented by the following general formula (1). Since the composition contains the phthalic anhydride derivative, it is improved in the adhesion between an adhesive layer and an adherend, thereby resulting in the improvement of durabilities such as heat resistance, water resistance and warm-water resistance.

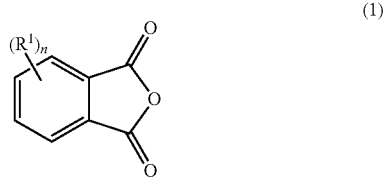

(1)

In the above general formula (1), $R^1$ is an alkyl group, an acyl group, an acyloxy group, an aryloxycarbonyl group, an aryl group, a hydroxyl group, a chlorine atom, a bromine atom or an iodine atom; and n is an integer of 1 to 4. $R^1$ is preferably an alkyl group having from 1 to 4 carbons, chlorine atom or bromine atom from the viewpoint of solubility to the 2-cyanoacrylic acid ester and stability and curability of the adhesive composition.

Examples of the specific compounds of the aforementioned general formula (1) include, for example, 3-methylphthalic anhydride, 4-methylphthalic anhydride, 4-tert-butylphthalic anhydride, 3-hydroxyphthalic anhydride, 4-hydroxyphthalic anhydride, 3-acetoxyphthalic anhydride, 4-benzoylphthalic anhydride, 4-phenethylphthalic anhydride, 4-phenoxycarbonylphthalic anhydride, 3-chlorophthalic anhydride, 4-chlorophthalic anhydride, 3-bromophthalic anhydride, 4-bromophthalic anhydride, 3-iodophthalic anhydride, 4-iodophthalic anhydride, 3,4-dichlorophthalic anhydride, 3,5-dichlorophthalic anhydride, 3,6-dichlorophthalic anhydride, 4,5-dichlorophthalic anhydride, 3,4-dibromophthalic anhydride, 3,5-dibromophthalic anhydride, 3,6-dibromophthalic anhydride, 4,5-dibromophthalic anhydride, 3,4-diiodophthalic anhydride, 3,5-diiodophthalic anhydride, 3,6-diiodophthalic anhydride, 4,5-diiodophthalic anhydride, 4-bromo-5-iodophthalic anhydride, 3,4,5-trichlorophthalic anhydride, 3,4,6-trichlorophthalic anhydride, 3,4,5-tribromophthalic anhydride, 3,4,6-tribromophthalic anhydride, 3,4,5-triiodophthalic anhydride, 3,4,6-triiodophthalic anhydride, tetrabromophthalic anhydride, tetrachlorophthalic anhydride and tetraiodophthalic anhydride.

The content of the aforementioned phthalic anhydride derivative is from 0.01 to 5% by mass relative to the total amount of the adhesive composition. The content is preferably from 0.05 to 4% by mass, and more preferably from 0.1 to 3% by mass. When the content is lower than 0.01% by mass, water resistance and warm-water resistance of the adhesive may not be improved. On the other hand, when the content exceeds 5% by mass, curability of the adhesive composition may be deteriorated.

The adhesive composition according to the present invention preferably comprises "(c) an elastomer" in addition to the above-mentioned components. When the elastomer is contained therein, durabilities such as heat resistance, water resistance and warm-water resistance are further improved.

The elastomer is preferably one having a rubbery elasticity around an ordinary temperature (20° C.±15° C.) or exhibiting a peak of loss tangent (tan δ) of dynamic viscoelasticity at a temperature not higher than 20° C. when measured at a frequency of 1 Hz, but is not limited as long as it is soluble in a 2-cyanoacrylic acid ester. As an elastomer that has a rubbery elasticity around an ordinary temperature (20° C.±15° C.), mention may be made of, for example, acrylate copolymers, acrylonitrile-styrene copolymers, acrylonitrile-styrene-acrylate copolymers, acrylonitrile-butadiene copolymers, acrylonitrile-butadiene-styrene copolymers, styrene-butadiene copolymers, styrene-isoprene copolymers, ethylene-acrylate copolymers, ethylene-propylene copolymers, ethylene-vinyl acetate copolymers, polyurethane copolymers, polyester copolymers, fluorinated copolymers, polyisoprene copolymers, and chloroprene copolymers. These may be used alone or in combination of two or more.

As an elastomer that exhibits a peak of loss tangent (tan δ) of dynamic viscoelasticity at a temperature not higher than 20° C. when measured at a frequency of 1 Hz, core-shell type elastomers can also be used. In the core-shell type elastomer, the polymer that constitutes the core and/or the shell has a glass transition point of preferably 20° C. or lower, and more preferably −10° C. or lower. As a monomer that forms the core phase of such a polymer, mention may be made of acrylic acid esters, and preferably acrylic acid esters having an alkyl group with 2 to 8 carbon atoms. On the other hand, the shell phase that forms the outermost layer is not particularly limited as long as it is a polymer component that is easily compatibilized with or dispersed in 2-cyanoacrylic acid ester, but is preferably a polymer component that can form an outermost layer of a glassy polymer having a glass transition point of 60° C. or more. As a monomer that forms the glassy polymer, mention may be made of, for example, methyl methacrylate and styrene.

Furthermore, preferred as the elastomer is a copolymer derived from a monomer capable of forming a polymer poorly soluble in 2-cyanoacrylic acid ester and a monomer capable of forming a polymer soluble in 2-cyanoacrylic acid ester (except the carboxyl-group containing monomers listed below). This copolymer comprises a poorly soluble segment formed by polymerization of the monomer capable of forming a polymer poorly soluble in 2-cyanoacrylic acid ester and a soluble segment formed by polymerization of the monomer capable of forming a polymer soluble in 2-cyanoacrylic acid ester.

The monomer capable of forming a polymer poorly soluble in 2-cyanoacrylic acid ester is not particularly limited, and examples thereof include ethylene, propylene, isoprene, butadiene, chloroprene, 1-hexene, cyclopentene, or the like. These monomers can be used alone or in a combination of two or more thereof. As the monomer capable of forming the poorly soluble polymer, often used are ethylene, propylene, isoprene, butadiene, and chloroprene; preferred is to use at least one selected from ethylene, propylene, isoprene, and butadiene.

The monomer capable of forming a polymer soluble in 2-cyanoacrylic acid ester also is not particularly limited, and examples thereof include acrylic acid esters, methacrylic acid esters, vinyl chloride, vinyl acetate, vinyl ether, styrene, acrylonitrile, or the like. Preferred is to use at least one of acrylic acid esters and methacrylic acid esters. Examples of the acrylic acid esters include methyl acrylate, ethyl acrylate, n-propyl acrylate, i-propyl acrylate, n-butyl acrylate, i-butyl acrylate, n-hexyl acrylate, n-heptyl acrylate, n-octyl acrylate, 2-ethylhexyl acrylate, methoxyethyl acrylate, methoxypropyl acrylate, ethoxyethyl acrylate, ethoxypropyl acrylate, or the like. These monomers can be used alone, or in a combination of two or more thereof.

Furthermore, examples of the methacrylic acid esters include methyl methacrylate, ethyl methacrylate, n-propyl methacrylate, i-propyl methacrylate, n-butyl methacrylate, i-butyl methacrylate, n-hexyl methacrylate, n-heptyl methacrylate, n-octyl methacrylate, 2-ethylhexyl methacrylate, methoxyethyl methacrylate, methoxypropyl methacrylate, ethoxyethyl methacrylate, ethoxypropyl methacrylate, or the like. These monomers can be used alone or in combination of two or more thereof. An acrylic acid ester and a methacrylic acid ester may be used in combination.

The proportion of the poorly soluble segment formed by polymerization of the monomer capable of forming the poorly soluble polymer and the soluble segment formed by polymerization of the monomer capable of forming the soluble polymer is not particularly limited so long as the poorly soluble segment accounts for 5 to 90 mol %, preferably 10 to 80 mol %, and the soluble segment accounts for 10 to 95 mol %, preferably 20 to 90 mol %, provided that the total of these segments is 100 mol %. More preferable proportion is from 30 to 80 mol % of the poorly soluble segment and from 20 to 70 mol % of the soluble segment; still preferable proportion is from 40 to 80 mol % of the poorly soluble segment and from 20 to 60 mol % of the soluble segment. Particularly preferable proportion is 50 to 75 mol % of the poorly soluble segment and from 25 to 50 mol % of the soluble segment. If the proportion of the poorly soluble segment is from 5 to 90 mol % and that of the soluble segment is from 10 to 95 mol %, particularly, if the proportion of the poorly soluble segment is from 30 to 80 mol % and that of the soluble segment is from 20 to 70 mol %, the copolymer can be properly dissolved in 2-cyanoacrylic acid ester to obtain an adhesive composition having excellent durability in addition to high shear adhesion strength or the like.

The proportion of the respective segments can be calculated by integration values for proton measured by proton nuclear magnetic resonance spectroscopy (referred to hereinafter as "$^1$H-NMR").

Further, among the above elastomers, particularly preferred is a copolymer that comprises a monomer capable of forming a polymer poorly soluble in 2-cyanoacrylic acid ester, a monomer capable of forming a polymer soluble in 2-cyanoacrylic acid ester, and a monomer containing a carboxyl group. In general, a small amount of the monomer containing a carboxyl group is added to the copolymer. The monomer containing a carboxyl group is not particularly limited, and examples thereof include acrylic acid, methacrylic acid, maleic acid, fumaric acid, itaconic acid, crotonic acid, cinnamic acid, or the like. These monomers can be used alone or in a combination of two or more thereof. Frequently used as the monomer containing a carboxyl group are acrylic acid and methacrylic acid, which may be used alone or in combination thereof. The segment containing a carboxyl group, which is formed by polymerization of the monomer containing a carboxyl group, is a highly hydrophilic segment soluble in 2-cyanoacrylic acid ester. When the elastomer is a copolymer having a carboxyl group, an adhesive composition exhibiting more excellent adhesion durability is provided.

The proportion of the segment containing a carboxyl group is not particularly limited, however, preferably, it is from 0.1 to 5 mol %, more preferably from 0.3 to 4 mol %, and further preferably from 0.4 to 3 mol %, provided that the total of the poorly soluble segment, the soluble segment, and the segment containing a carboxyl group is 100 mol %. The proportion is further preferably from 0.5 to 2.5 mol %, and particularly preferably from 0.5 to 2.3 mol %. So long as the segment containing a carboxyl group is contained in a range of from 0.1 to 5 mol %, particularly preferably from 0.5 to 2.3 mol %, an adhesive composition can be provided, which quickly hardens after application to adherends and possesses excellent resistance to warm water.

The proportion of the segment containing a carboxyl group can be measured by potentiometric titration or by indicator titration in accordance with JIS K 0070.

Examples of the copolymer include an ethylene/methyl acrylate copolymer, an ethylene/methyl acrylate/butyl acrylate copolymer, an ethylene/methyl methacrylate copolymer, an ethylene/vinyl acetate copolymer, a butadiene/methyl acrylate copolymer, a butadiene/acrylonitrile copolymer, a butadiene/acrylonitrile/acrylic acid ester copolymer, and a butadiene/styrene/acrylonitrile/methyl acrylate copolymer. Particularly preferred copolymers among them are an ethylene/methyl acrylate copolymer and an ethylene/methyl acrylate/butyl acrylate copolymer. A copolymer resulting from polymerization of monomers used in the above respective copolymers with a monomer containing a carboxyl group, such as acrylic acid and/or methacrylic acid, for example, ethylene/methyl acrylate/acrylic acid copolymer, ethylene/methyl acrylate/methacrylic acid copolymer, ethylene/methyl acrylate/butyl acrylate/acrylic acid copolymer, ethylene/methyl acrylate/butyl acrylate/methacrylic acid copolymer or the like, is also usable. These copolymers may be used alone or in a combination of two or more thereof, or a copolymer formed without the monomer containing a carboxyl group may be used in combination with a copolymer formed with the monomer containing a carboxyl group.

The average molecular weight of the elastomer is not particularly limited, however, the number average molecular weight (Mn) is preferably in a range of from 5000 to 500000, particularly preferably from 15000 to 150000, and further preferably from 20000 to 100000. So long as the elastomer has a number average molecular weight in the range of from 5000 to 500000, the elastomer easily dissolves in 2-cyanoacrylic acid ester, and particularly an adhesive composition maintaining high adhesion strength after the warm-water resistance test can be obtained. Further, the weight average molecular weight (Mw) of the elastomer is preferably in a range of from 5000 to 1000000, particularly from 10000 to 1000000, and Mw/Mn is preferably in a range of from 1.00 to 10.0, and particularly from 1.00 to 8.0.

The content of the aforementioned elastomer is preferably in the range of from 1 to 30% by mass relative to the total amount of the adhesive composition. Although depending on the type of the 2-cyanoacrylic acid ester, the content of the aforementioned elastomer is more preferably from 2 to 20% by mass, and further preferably from 3 to 15% by mass. So long as the content of the elastomer is in the range of from 1 to 30% by mass, an adhesive composition possessing an excellent durability can be provided whilst the adhesive composition is not greatly deteriorated in curability.

In addition to the aforementioned components, the adhesive composition according to the present invention may arbitrarily contain anion polymerization accelerators, stabilizers, plasticizers, thickeners, fumed silica, particles, fillers, colorants, fragrances, solvents, strength improvers and the like that have conventionally been blended in the adhesive composition containing a 2-cyanoacrylic acid ester, according to purposes and in proper quantities within the ranges that do not impair curability, adhesion strength or the like.

Examples of the anion polymerization accelerators include polyalkylene oxides, crown ethers, silacrown ethers, calixarenes, cyclodextrins, and pyrogallol-based cyclic compounds. The polyalkylene oxides refer to polyalkylene oxides and the derivatives thereof, and examples thereof include those disclosed in Japanese Patent Publication (Kokoku) No. S60-37836, Japanese Patent Publication (Kokoku) No. H1-43790, Japanese Patent Publication (Laid-Open) No. S63-128088, Japanese Patent Publication (Laid-Open) No. H3-167279, U.S. Pat. Nos. 4,386,193, and 4,424,327. Concrete examples thereof include (1) polyalkylene oxides such as diethylene glycol, triethylene glycol, polyethylene glycol, and polypropylene glycol; and (2) derivatives of polyalkylene oxides such as polyethylene glycol monoalkyl esters, polyethylene glycol dialkyl esters, polypropylene glycol dialkyl esters, diethylene glycol monoalkyl ethers, diethylene glycol dialkyl ethers, dipropylene glycol monoalkyl ethers, and dipropylene glycol dialkyl ethers. Examples of the crown ethers include those disclosed in, for instance, Japanese Patent Publication (Kokoku) No. S55-2236 and Japanese Patent Publication (Laid-Open) No. H3-167279. Concrete examples thereof include 12-crown-4, 15-crown-5, 18-crown-6, benzo-12-crown-4, benzo-15-crown-5, benzo-18-crown-6, dibenzo-18-crown-6, dibenzo-24-crown-8, dibenzo-30-crown-10, tribenzo-18-crown-6, asym-dibenzo-22-crown-6, dibenzo-14-crown-4, dicyclohexyl-24-crown-8, cyclohexyl-12-crown-4, 1,2-decalyl-15-crown-5, 1,2-naphtho-15-crown-5, 3,4,5-naphthyl-16-crown-5, 1,2-methylbenzo-18-crown-6, 1,2-tert-butyl-18-crown-6, and 1,2-vinylbenzo-15-crown-5. Examples of the silacrown ethers include, for example, those disclosed in Japanese Patent Publication (Laid-Open) No. S60-168775. Concrete examples thereof include dimethylsila-11-crown-4, dimethylsila-14-crown-5, and dimethylsila-17-crown-6. Examples of the calixarenes include those disclosed in Japanese Patent Publication (Laid-Open) No. S60-179482, Japanese Patent Publication (Laid-Open) No. S62-235379, and Japanese Patent Publication (Laid-Open) No. S63-88152. Concrete examples thereof include 5,11,17,23,29,35-hexa-tert-butyl-37,38,39,40,41,42-hexahydroxycalix[6]arene, 37,38,39,40,41,42-hexahydroxycalix[6]arene, 37,38,39,40,41,42-hexa-(2-oxo-2-ethoxy)-ethoxycalix[6]arene, 25,26,27,28-tetra-(2-oxo-2-ethoxy)-ethoxycalix[4]arene, and tetrakis(4-t-butyl-2-methylenephenoxy)ethyl acetate. Examples of the cyclodextrins include those disclosed in Japanese Patent Publication (Kohyo) No. H5-505835. Concrete examples thereof include α-, β-, or γ-cyclodextrins. Examples of the pyrogallol-based cyclic compounds include compounds disclosed in Japanese Patent Publication (Laid-Open) No. 2000-191600. Concrete examples thereof include 3,4,5,10,11,12,17,18,19,24,25,26-dodecaethoxycarbomethoxy-C-1,C-8,C-15,C-22-tetramethyl[14]-metacyclophane. These anion polymerization accelerators may be used alone or in combination of two or more thereof.

The stabilizers include (1) anion polymerization inhibitors, such as sulfur dioxide, aliphatic sulfonates such as methanesulfonate, aromatic sulfonates such as p-toluenesulfonate, boron trifluoride complexes such as boron trifluoride methanol and boron trifluoride diethyl ether, $HBF_4$, and trialkyl borate; and (2) radical polymerization inhibitors such as hydroquinone, hydroquinone monomethyl ether, t-butylcatechol, catechol, and pyrogallol. These stabilizers may be used alone, or in a combination of two or more thereof.

A plasticizer may be incorporated so long as the effect of the invention is not impaired; in particular, when the elastomer is constituted by a copolymer resulting from the use of a larger amount of monomers capable of forming the poorly soluble polymers, i.e., a copolymer containing a larger amount of the poorly soluble segments (a copolymer containing 65 mol % or more of the poorly soluble segments), the addition of the plasticizer in a proper quantity improves the solubility thereof. The plasticizer includes triethyl acetyl citrate, tributyl acetyl citrate, dimethyl adipate, diethyl adipate, dimethyl sebacate, dimethyl phthalate, diethyl phthalate, dibutyl phthalate, diisodecyl phthalate, dihexyl phthalate, diheptyl phthalate, dioctyl phthalate, bis(2-ethylhexyl) phthalate, diisononyl phthalate, diisotridecyl phthalate, dipentadecyl phthalate, dioctyl terephthalate, diisononyl isophthalate, decyl toluate, bis(2-ethylhexyl) camphorate, 2-ethylhexylcyclohexyl carboxylate, diisobutyl fumarate, diisobutyl maleate, caproic triglyceride, 2-ethylhexyl benzoate, and dipropylene glycol dibenzoate. Among them, preferred from the viewpoint of good compatibility with 2-cyanoacrylic acid ester and of high plasticizing efficiency are tributyl acetyl citrate, dimethyl adipate, dimethyl phthalate, 2-ethylhexyl benzoate, and dipropylene glycol dibenzoate. These plasticizers may be used alone or in combination of two or more thereof. The content of the plasticizers is not particularly limited, however, the range thereof is preferably from 3 to 50% by mass, particularly preferably from 10 to 45% by mass, and further preferably from 20 to 40% by mass relative to the total amount of the adhesive composition. So long as the content of the plasticizer is in a range of from 3 to 50% by mass, the copolymer can be easily dissolved in 2-cyanoacrylic acid ester, and particularly the retention rate of the adhesive strength after warm-water resistance test can be improved, especially when a copolymer containing a large amount of a poorly soluble segments (a copolymer containing 65 mol % or more of a poorly soluble segments) is used as the elastomer.

Further, the thickeners include polymethyl methacrylates, copolymers of methyl methacrylate and an acrylate, copolymers of methyl methacrylate and another methacrylate, acrylic rubbers, polyvinylchloride, polystyrene, cellulose esters, polyalkyl-2-cyanoacrylate, and ethylene-vinyl acetate copolymers. These thickeners may be used alone or in combination of two or more thereof. The content of the thickener is not particularly limited, but is preferably from 0.1 to 20% by mass, and more preferably from 0.5 to 15% by mass relative to the total amount of the adhesive composition.

The adhesive composition may contain fumed silica. The fumed silica refers to ultrafine anhydrous silica (having a primary particle size of 500 nm or smaller, particularly from 1 to 200 nm). This anhydrous silica is ultrafine anhydrous silica (having a primary particle size of 500 nm or smaller, particularly from 1 to 200 nm) which is obtained by, for example, oxidizing silicon tetrachloride as a starting material in gas phase under a high temperature flame, and includes hydrophilic silica which has high hydrophilicity, and hydrophobic silica which has high hydrophobicity. Either of the fumed silica is usable, however, preferred is hydrophobic silica from the viewpoint of dispersibility in 2-cyanoacrylic acid ester. Furthermore, it is preferred that a hydrophilic silica is used in combination when a copolymer resulting from use of a larger amount of monomers capable of forming polymers soluble in 2-cyanoacrylic acid ester, i.e., a copolymer containing a larger amount of the soluble segments (which include segments containing a carboxyl group) is used as the elastomer, and a hydrophobic silica is used in combination when a copolymer resulting from use of a larger amount of monomers capable of forming the poorly soluble polymer, i.e., a copolymer containing a larger amount of the poorly soluble segments (a copolymer containing 65 mol % or more of the poorly soluble segments) is used as the elastomer.

Various types of commercially available products can be used as hydrophilic silica; such as AEROSIL50, 130, 200, 300, and 380 (trade names, manufactured by Nippon Aerosil Co., Ltd.). The specific surface areas of the above hydrophilic silicas are 50±15 m$^2$/g, 130±25 m$^2$/g, 200±25 m$^2$/g, 300±30 m$^2$/g, and 380±30 m$^2$/g, respectively. Another usable commercially available hydrophilic silica products include REOLOSIL QS-10, QS-20, QS-30, QS-40 (trade names, manufactured by Tokuyama Corporation), and the like. These hydrophilic silicas have a specific surface area of 140±20 m$^2$/g, 220±20 m$^2$/g, 300±30 m$^2$/g, and 380±30 m$^2$/g, respectively. In addition to above, commercially available hydrophilic silicas manufactured by Cabot Corporation and the like can also be used. The specific surface area of the hydrophilic silica is preferably from 20 to 600 m$^2$/g.

Further, as hydrophobic silica, products which are made hydrophobic by treating a surface of hydrophilic silica can be also used. Examples of the method for obtaining hydrophobic silica by conducting surface treatment of hydrophilic silica include a method in which a compound capable of forming a hydrophobic group by reaction with the hydroxyl group that is present on the surface of the hydrophilic silica, or a compound which is adsorbed by the surface of the hydrophilic silica to form a hydrophobic layer thereon, is brought into contact with the hydrophilic silica in the presence or absence of a solvent, preferably, with heating.

The compounds for use in surface treatment of the hydrophilic silica to render it hydrophobic include various types of alkyl-, aryl-, and aralkyl-based silane coupling agents having hydrophobic groups, such as n-octyl trialkoxysilane and the like; silylating agents such as methyltrichlorosilane, dimethyldichlorosilane, and hexamethyldisilazane; silicone oils such as polydimethylsiloxane and the like; higher alcohols such as stearyl alcohol and the like; and higher fatty acids such as stearic acid and the like. Any of the products rendered hydrophobic using the above compounds can be used as the hydrophobic silica.

Examples of the commercially available hydrophobic silica include AEROSIL RY200 and R202, which are rendered hydrophobic by surface treatment using silicone oil; AEROSIL R974, R972, and R976, which are rendered hydrophobic by surface treatment using a dimethylsilylating agent; AEROSIL R805, which is rendered hydrophobic by surface treatment using n-octyltrimethoxysilane; AEROSIL R811 and R812, which are rendered hydrophobic by surface treatment using a trimethylsilylating agent (wherein the above products under the trade name AEROSIL are all manufactured by Nippon Aerosil Co., Ltd.); and REOLOSIL MT-10 (trade name, manufactured by Tokuyama Corporation), which is rendered hydrophobic by surface treatment using methyltrichlorosilane. The specific surface areas of these hydrophobic silicas are 100±20 m$^2$/g, 100±20 m$^2$/g, 170±20 m$^2$/g, 110±20 m$^2$/g, 250±25 m$^2$/g, 150±20 m$^2$/g, 150±20 m$^2$/g, 260±20 m$^2$/g, and 120±10 m$^2$/g, respectively. The specific surface area of the hydrophobic silica is preferably from 20 to 400 m$^2$/g.

A preferred content of the fumed silica in the adhesive composition is from 1 to 30% by mass relative to the total amount of the adhesive composition. A further preferred content of the fumed silica depends on the type of the 2-cyanoacrylic acid ester, the types and proportion of the monomers used for the production of the elastomer, the type of the fumed silica and the like, but is from 1 to 25% by mass, and particularly preferably from 2 to 20% by mass. When the content of the fumed silica is from 1 to 30% by mass, an adhesive composition good in workability can be provided without impairing curability, adhesion strength or the like.

EXAMPLES

The present invention is explained in detail by way of Examples and Comparative Examples below, but the present invention is not particularly limited thereby. The skilled in the art can perform various changes, modifications and alterations without deviating from the scope of the present invention. In the description below, parts and percentages are based on mass unless otherwise mentioned.

1. Evaluation Method
(1) Adhesion Rate

The adhesion rate was measured at 23° C. under 60% RH with test pieces described in JIS K 6861 "Testing methods for α-cyanoacrylate adhesives", Section 7.1.3, bonded together using each adhesive composition. The material of the test pieces used in the measurement was as follows:

Test piece: Aluminum (material designated in JIS A6063S).

(2) Impact Peel Adhesion Strength

The impact peel adhesion strength was measured at 23° C. under 50% RH in accordance with JIS K 6855 "Testing methods for impact peel adhesion strength of adhesives". The material of the test pieces used in the measurement was as follows:

Test piece: Iron (material designated in JIS SGD400D).

(3) Water Resistance and Warm-Water Resistance

Test pieces described in JIS K 6861 "Testing methods for α-cyanoacrylate adhesives", Section 7.1.3, were bonded together at 23° C. under 60% RH using each adhesive composition, and were allowed to stand still for curing at a temperature of 23° C. for a day. Then, tensile adhesion strength (which is referred to as "initial strength") was measured in accordance to JIS K 6861. Then, after immersing the test pieces in warm water at 23° C. or 74° C. for 7 days, tensile adhesion strength (referred to as "post test strength") was measured, and the retention rate was calculated according to the following equation.

Retention rate (%)=(post test strength/initial strength)×100

The material of the test pieces used in the measurement was as follows:

Test piece: Aluminum (material designated in JIS A6063S).

2. Production of 2-Cyanoacrylate Adhesive Composition (1) Example 1

To ethyl 2-cyanoacrylate, were blended 20 ppm of sulfur dioxide and 1000 ppm of hydroquinone (provided that ethyl 2-cyanoacrylate was 100 parts by mass). Then, 0.5% of tetrachlorophthalic anhydride and 4% of polymethylmethacrylate relative to the total amount of the adhesive composition were added and dissolved under stirring at 23° C. for an hour to produce an adhesive composition. The results are shown in Table 2.

(2) Examples 2 to 11 and Comparative Examples 1 to 8

Adhesive compositions were prepared in the same manner as in Example 1, except that the additive, the elastomer, the thickener, and the fumed silica as shown in Table 1 were added to the adhesive compositions. The results are given in Table 2.

TABLE 1

|  | Additive | | Elastomer | | Thickener | | Fumed Silica | |
| --- | --- | --- | --- | --- | --- | --- | --- | --- |
|  | Type | Content (%) | Type | Content (%) | Type | Content (%) | Type | Content (%) |
| Ex. 1 | Tetrachlorophthalic anhydride | 0.5 | — | | PMMA | 4 | — | |
| Ex. 2 | 4-methylphthalic anhydride | 0.5 | — | | PMMA | 4 | — | |
| Ex. 3 | 4-bromophthalic anhydride | 0.5 | — | | PMMA | 4 | — | |
| Ex. 4 | 4-methylphthalic anhydride | 0.25 | — | | — | | — | |
| Ex. 5 | 4-methylphthalic anhydride | 0.5 | — | | — | | — | |
| Ex. 6 | 4-methylphthalic anhydride | 1 | — | | — | | — | |
| Ex. 7 | 4-methylphthalic anhydride | 0.5 | ASA | 4 | — | | — | |
| Ex. 8 | 4-methylphthalic anhydride | 0.5 | ASA | 8 | — | | — | |
| Ex. 9 | 4-methylphthalic anhydride | 0.5 | ASA | 12 | — | | — | |
| Ex. 10 | 4-methylphthalic anhydride | 0.5 | ASA | 4 | — | | RY200 | 4 |
| Ex. 11 | 4-methylphthalic anhydride | 0.5 | Vamac DP | 4 | — | | RY200 | 4 |
| Comp. Ex. 1 | | | — | | — | | — | |
| Comp. Ex. 2 | Aconitic acid | 0.02 | — | | — | | — | |
| Comp. Ex. 3 | | | — | | PMMA | 4 | — | |
| Comp. Ex. 4 | | | ASA | 4 | — | | — | |
| Comp. Ex. 5 | Aconitic acid | 0.02 | — | | PMMA | 4 | — | |
| Comp. Ex. 6 | Phthalic anhydride | 0.5 | — | | PMMA | 4 | — | |
| Comp. Ex. 7 | 1,8-naphthalic anhydride | 0.5 | — | | PMMA | 4 | — | |
| Comp. Ex. 8 | cis-4-cyclohexene-1,2-dicarboxylic anhydride | 0.5 | — | | PMMA | 4 | — | |

Abbreviations in Table 1 indicate the following materials.

<Elastomer>

ASA: "DIALAC 5510" (tradename) (acrylonitrile/butadiene/butyl acrylate/styrene copolymer) manufactured by UMG ABS Ltd.

Vamac DP: "Vamac DP" (trade name) (ethylene/methyl acrylate copolymer) manufactured by DuPont <Thickener>

PMMA: Polymethylmethacrylate, molecular weight of 1,000,000

<Fumed Silica>

RY200: "AEROSIL1 RY200" (tradename) manufactured by Nippon Aerosil Co., Ltd. (hydrophobic silica, specific surface area of 100±20 m2/g)

TABLE 2

| | Adhesion rate (seconds) | Impact peel strength (kJ/m²) | Water resistance tensile adhesion strength (N/mm²) | | | | |
|---|---|---|---|---|---|---|---|
| | | | Initial | 23° C. water × 7 days | Retention Rate | 74° C. water × 7 days | Retention Rate |
| Ex. 1 | ≤3 | >30 | 28 | 27 | 96% | 11 | 39% |
| Ex. 2 | ≤3 | >30 | 32 | 31 | 97% | 10 | 31% |
| Ex. 3 | ≤3 | >30 | 30 | 25 | 83% | 10 | 33% |
| Ex. 4 | ≤3 | >30 | 29 | 28 | 97% | 11 | 38% |
| Ex. 5 | ≤3 | >30 | 32 | 30 | 94% | 12 | 38% |
| Ex. 6 | ≤3 | >30 | 29 | 27 | 93% | 13 | 45% |
| Ex. 7 | ≤3 | >30 | 35 | No evaluation | | 12 | 34% |
| Ex. 8 | ≤3 | >30 | 32 | No evaluation | | 13 | 41% |
| Ex. 9 | ≤3 | >30 | 25 | No evaluation | | 15 | 60% |
| Ex. 10 | ≤5 | >30 | 27 | No evaluation | | 13 | 48% |
| Ex. 11 | ≤5 | >30 | 20 | No evaluation | | 16 | 80% |
| Comp. Ex. 1 | ≤3 | 16 | 26 | 10 | 38% | 3 | 12% |
| Comp. Ex. 2 | ≤3 | >30 | 35 | 18 | 51% | 3 | 9% |
| Comp. Ex. 3 | ≤3 | 18 | 28 | 11 | 39% | 3 | 11% |
| Comp. Ex. 4 | ≤3 | >30 | 23 | 9 | 39% | 4 | 17% |
| Comp. Ex. 5 | ≤3 | >30 | 33 | 16 | 48% | 4 | 12% |
| Comp. Ex. 6 | ≤3 | >30 | 32 | 31 | 97% | 5 | 16% |
| Comp. Ex. 7 | ≤3 | >30 | 25 | 13 | 52% | 5 | 20% |
| Comp. Ex. 8 | ≤3 | >30 | 32 | 20 | 63% | 6 | 19% |

According to the results of Table 2, it was found that the adhesive compositions of Examples 1 to 6 were excellent in water resistance and warm-water resistance without impairing instantaneous adhesiveness. Moreover, the adhesive compositions of Examples 7 to 11 were also excellent in warm-water resistance. On the other hand, the adhesive compositions of Comparative Examples 1 to 5, 7 and 8, which contained no specific phthalic anhydride derivative, were deteriorated in water resistance and warm-water resistance. Further, Comparative Example 6 which contained phthalic anhydride maintained adhesion strength in the evaluation of water resistance, but was greatly deteriorated in adhesion strength in the evaluation of warm-water resistance.

INDUSTRIAL APPLICABILITY

The 2-cyanoacrylate adhesive composition of the present invention can be utilized as a so-called instantaneous adhesive in a wide range of products in a broad range of fields including industrial, medical and household applications. It is particularly useful for applications in which water resistance and warm-water resistance are required.

The invention claimed is:
1. A 2-cyanoacrylate adhesive composition which comprises (a) a 2-cyanoacrylic acid ester, and (b) a phthalic anhydride derivative represented by the following general formula (1), in which a content of the phthalic anhydride derivative is from 0.01 to 5% by mass relative to the total amount of the adhesive composition

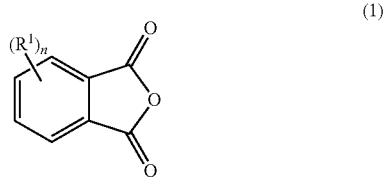

(1)

wherein R¹ is an alkyl group having from 1 to 4 carbon atoms, chlorine atom, or bromine atom, and n represents an integer of 1 to 4.

2. The 2-cyanoacrylate adhesive composition according to claim 1, which further comprises (c) an elastomer, wherein a content of the elastomer is from 1 to 30% by mass relative to the total amount of the adhesive composition.

3. The 2-cyanoacrylate adhesive composition according to claim 2, wherein the elastomer (c) is a copolymer made from a monomer that is at least one selected from the group consisting of ethylene, propylene, isoprene, butadiene, chloroprene, 1-hexene and cyclopentene, and a monomer capable of forming a polymer soluble to 2-cyanoacrylic acid ester.

4. The 2-cyanoacrylate adhesive composition according to claim 2, wherein the elastomer (c) is a copolymer made from a monomer that is at least one selected from the group consisting of ethylene, propylene, isoprene, butadiene, chloroprene, 1-hexene and cyclopentene, a monomer capable of forming a polymer soluble to 2-cyanoacrylic acid ester, and a monomer containing a carboxyl group.

5. The 2-cyanoacrylate adhesive composition according to claim 2, wherein the elastomer (c) is a copolymer made from a monomer that is at least one selected from the group consisting of ethylene, propylene, isoprene and butadiene, and a monomer that is at least one selected from the group consisting of acrylic acid esters and methacrylic acid esters.

6. The 2-cyanoacrylate adhesive composition according to claim 2, wherein the elastomer (c) is a copolymer made from a monomer that is at least one selected from the group consisting of ethylene, propylene, isoprene and butadiene, and a monomer that is at least one selected from the group consisting of acrylic acid esters and methacrylic acid esters, and a monomer containing a carboxyl group.

7. The 2-cyanoacrylate adhesive composition according to claim 1, wherein the content of the phthalic anhydride derivative is from 0.1 to 44% by mass relative to the total amount of the adhesive composition.

8. The 2-cyanoacrylate adhesive composition according to claim 1, wherein the content of the phthalic anhydride derivative is from 0.25 to 1% by mass relative to the total amount of the adhesive composition.

9. The 2-cyanoacrylate adhesive composition according to claim 1, wherein R¹ is methyl and n is 1.

10. The 2-cyanoacrylate adhesive composition according to claim 8, wherein R¹ is methyl and n is 1.

11. The 2-cyanoacrylate adhesive composition according to claim 1, wherein $R^1$ an alkyl group having from 1 to 4 carbons.

12. The 2-cyanoacrylate adhesive composition according to claim 11, wherein n is 1.

13. The 2-cyanoacrylate adhesive composition according to claim 1, wherein n is 1 and $R^1$ is a 4-alkyl group having from 1 to 4 carbon atoms.

14. The 2-cyanoacrylate adhesive composition according to claim 13, wherein the phthalic anhydride derivative is 4-methyl phthalic anhydride.

15. The 2-cyanoacrylate adhesive composition according to claim 7, wherein $R^1$ is methyl and n is 1.

16. The 2-cyanoacrylate adhesive composition according to claim 14, wherein the content of the phthalic anhydride derivative is from 0.1 to 4% by mass relative to the total amount of the adhesive composition.

17. The 2-cyanoacrylate adhesive composition according to claim 14, wherein the content of the phthalic anhydride derivative is from 0.1 to 3% by mass relative to the total amount of the adhesive composition.

18. The 2-cyanoacrylate adhesive composition according to claim 1, wherein the content of the phthalic anhydride derivative is from 0.1 to 3% by mass relative to the total amount of the adhesive composition.

19. The 2-cyanoacrylate adhesive composition according to claim 18, wherein $R^1$ is methyl and n is 1.

20. The 2-cyanoacrylate adhesive composition according to claim 14, wherein the content of the phthalic anhydride derivative is from 0.25 to 1% by mass relative to the total amount of the adhesive composition.

* * * * *